(12) United States Patent
Mann et al.

(10) Patent No.: US 8,859,465 B2
(45) Date of Patent: Oct. 14, 2014

(54) SYNERGISTIC HERBICIDAL COMPOSITION CONTAINING PENOXSULAM AND GLUFOSINATE-AMMONIUM

(71) Applicant: Dow AgroSciences LLC, Indianapolis, IN (US)

(72) Inventors: Richard K. Mann, Franklin, IN (US); Yi-hsiou Huang, Pingtung Hsieng (TW)

(73) Assignee: Dow AgroSciences, LLC., Indianapolis, IN (US)

( * ) Notice: Subject to any disclaimer, the term of this patent is extended or adjusted under 35 U.S.C. 154(b) by 10 days.

(21) Appl. No.: 13/688,615

(22) Filed: Nov. 29, 2012

(65) Prior Publication Data

US 2013/0137576 A1    May 30, 2013

Related U.S. Application Data

(60) Provisional application No. 61/565,076, filed on Nov. 30, 2011.

(51) Int. Cl.
| | | |
|---|---|---|
| *A01N 57/10* | (2006.01) | |
| *A01N 43/90* | (2006.01) | |
| *A01N 41/02* | (2006.01) | |
| *A01N 43/00* | (2006.01) | |
| *A01N 57/20* | (2006.01) | |

(52) U.S. Cl.
   CPC ..................... *A01N 57/20* (2013.01)
   USPC .......................................... 504/128; 504/136

(58) Field of Classification Search
   USPC .................. 504/128, 118, 127, 139, 241, 136
   See application file for complete search history.

(56) References Cited

U.S. PATENT DOCUMENTS

| | | |
|---|---|---|
| 5,858,924 A | 1/1999 | Johnson et al. |
| 2006/0183637 A1 | 8/2006 | Loughner et al. |
| 2009/0029857 A1 | 1/2009 | Meazza et al. |
| 2011/0287932 A1 * | 11/2011 | Hacker et al. ............... 504/103 |
| 2011/0287934 A1 * | 11/2011 | Hacker et al. ............... 504/105 |

FOREIGN PATENT DOCUMENTS

WO    WO2007053482 A2    5/2007

OTHER PUBLICATIONS

Disclosed Anonymously 462055: "2-(2,2-difluoroethoxy)-6-trifluoromethyl-N-(5,8-dimethoxy[1,2,4]triazolo[1,5-c] pyrimidin-2-yl )benzenesulfonamide and its use as a herbicide in mixtures" Research Disclosure, Oct. 2002, pp. 1832-1833.

"Penoxsulam and Its Use as a Herbicide in Mixtures for Use in Rice, Wheat, Barely, Oats, Sorghum, Corn, Maize, Ivm, Rangeland Pastures, Grasslands, Fallowland, Turf, and Aquatics" The IP.com Journal, vol. 5, No. 4, Apr. 2005, pp. 286-293.

* cited by examiner

*Primary Examiner* — John Pak
*Assistant Examiner* — Andriae M Holt
(74) *Attorney, Agent, or Firm* — Robert Chang

(57) ABSTRACT

A synergistic mixture of penoxsulam and glufosinate-ammonium controls weeds in crops, e.g., vineyards, orchards, perennial plantation crops, rice, corn, cereals, sorghum, soybeans, cotton, sunflower, oilseed rape, vegetables, turf, range and pasture, industrial vegetation management (IVM), rights-of-way and in any glufosinate-ammonium and/or ALS (acetolactate synthase)-tolerant crops.

20 Claims, No Drawings

SYNERGISTIC HERBICIDAL COMPOSITION CONTAINING PENOXSULAM AND GLUFOSINATE-AMMONIUM

CROSS REFERENCE TO RELATED APPLICATIONS

This application claims the benefit of U.S. Provisional Patent Application Ser. No. 61/565,076 filed Nov. 30, 2011.

FIELD

This disclosure concerns a synergistic herbicidal composition containing (a) penoxsulam and (b) glufosinate or a salt or ester thereof, e.g. glufosinate-ammonium for controlling the growth of undesirable vegetation, e.g. in vineyards, orchards, perennial plantation crops, rice, corn, cereals, sorghum, soybeans, cotton, sunflower, oilseed rape, vegetables, turf, range and pasture, industrial vegetation management (IVM), rights-of-way and in any glufosinate-ammonium and/or ALS (acetolactate synthase)-tolerant crops, including but not limited to vineyards, orchards, rice, corn, cereals, sorghum, soybeans, cotton, sunflower, oilseed rape, turf and vegetable crops. These compositions provide improved herbicidal weed control.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429 "'synergism' [is] an interaction of two or more factors such that the effect when combined is greater than the predicted effect based on the response to each factor applied separately." The present disclosure is based on the discovery that penoxsulam and glufosinate-ammonium, already known individually for their herbicidal efficacy, display a synergistic effect when applied in combination.

SUMMARY

The present disclosure concerns a synergistic herbicidal mixture comprising a herbicidally effective amount of (a) penoxsulam and (b) glufosinate or a salt or ester thereof, e.g. glufosinate-ammonium. The compositions may also contain an agriculturally acceptable adjuvant and/or carrier.

The present disclosure also concerns herbicidal compositions for and methods of controlling the growth of undesirable vegetation, particularly in vineyards, orchards, perennial plantation crops, rice, corn, cereals, sorghum, soybeans, cotton, sunflower, oilseed rape, vegetables, turf, vegetable crops, range and pasture, industrial vegetation management (IVM), rights-of-way and in any glufosinate-ammonium and/or ALS (acetolactate synthase)-tolerant crops, and the use of these synergistic compositions.

The species spectra of penoxsulam and glufosinate-ammonium, i.e., the weed species which the respective compounds control, are broad and highly complementary. It has now been found that in certain embodiments, the compositions provided herein exhibit a synergistic action in the control of barnyardgrass (*Echinochloa crus-galli*, ECHCG), smallflower umbrella sedge (*Cyperus difformis*, CYPDI), monochoria (*Monochoria vaginalis*, MOOVA) and Japanese bulrush (*Schoenoplectus juncoides*, SCPJU) at application rates equal to or lower than the rates of the individual compounds.

DETAILED DESCRIPTION

Penoxsulam is the common name for 2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in The Pesticide Manual, Fifteenth Edition, 2009. Penoxsulam controls *Echinochloa* spp., as well as many broadleaf, sedge and aquatic weeds in rice, and *Apera* spp. grass in cereals, as well as many broadleaf weeds in aquatics, tree and vine crops, cereal crops, range and pasture, IVM and turf.

Glufosinate is the common name for 2-amino-4-(hydroxymethylphosphinyl)butanoic acid. Its herbicidal activity is described in *The Pesticide Manual*, Fifteenth Edition, 2009. An exemplary salt of glufosinate is glufosinate-ammonium, which has been used for control of a wide range of annual and perennial broadleaf weeds and grasses in fruit orchards, vineyards, rubber and oil palm plantations, ornamental trees and bushes, non-crop land, and glufosinate-tolerant crops.

The term herbicide is used herein to mean an active ingredient that kills, controls or otherwise adversely modifies the growth of plants. A herbicidally effective or vegetation-controlling amount is an amount of active ingredient which causes an adversely modifying effect, which includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds when they are applied directly to the plant or to the locus of, i.e., area adjacent to the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature, undesirable vegetation to achieve the maximum control of weeds.

In some embodiments, the compositions and methods provided herein are utilized to control weeds in the presence of crops or in other settings, including but not limited to direct-seeded, water-seeded and transplanted rice, vineyards, orchards, perennial plantation crops, corn, cereals, sorghum, soybeans, cotton, sunflower, oilseed rape, vegetables, turf, range and pasture, industrial vegetation management (IVM), rights-of-way and in any glufosinate-ammonium and/or ALS (acetolactate synthase)-tolerant crops. In certain embodiments, the methods and compositions described herein do not injure or significantly injure the crops.

In certain embodiments, the compositions and methods provided herein are utilized to control weeds in rice. In certain embodiments, the rice is dry-seeded, wet-seeded, water-seeded, or transplanted rice.

The compositions and methods described herein can be used to control undesirable vegetation in glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant-, and bromoxynil-tolerant-crops (such as, but not limited to, soybean, cotton, canola/oilseed rape, rice, cereals, corn, turf, etc.), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, penoxsulam and glufosinate-ammonium or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

The compositions and methods provided herein are utilized to control undesirable vegetation. Undesirable vegetation includes, but is not limited to, undesirable vegetation that occurs in rice, vineyards, orchards, perennial plantation crops, corn, cereals, sorghum, soybeans, cotton, sunflower, oilseed rape, vegetables, turf, range and pasture, industrial vegetation management (IVM) and rights-of-way.

In some embodiments of the methods described herein, the penoxsulam and glufosinate are applied simultaneously or in the form of the compositions described herein. In some embodiments, the penoxsulam and glufosinate are applied sequentially, e.g., within 5, 10, 15, or 30 minutes of each other; 1, 2, 3, 4, 5, 10, 12, 24, 48 hour(s) or each other, or 1 week of each other.

In some embodiments, the methods provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, IVM and rights of way. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in tree and vine, perennial crops and row crops, including but not limited to vineyards, orchards, perennial plantation crops, corn, sorghum, soybeans, cotton, sunflower, oilseed rape and vegetables. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), Sinapis arvensis L. (wild mustard, SINAR), *Solanum ptychanthum* Dunal (eastern black nightshade, SOLPT), or *Xanthium strumarium* L. (common cocklebur, XANST).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Cyperus, Echinochloa, Monochoria* and *Schoenoplectus*.

In some embodiments, the combination of (a) penoxsulam and (b) glufosinate-ammonium or agriculturally acceptable salt or ester thereof are used to control *Cyperus difformis* L. (smallflower umbrella sedge, CYPDI), *Echinochloa crus-galli* (L.) Beauv. (barnyardgrass, ECHCG), monochoria (*Monochoria vaginalis*, MOOVA) and *Schoenoplectus juncoides* (Roxb.) Palla (Japanese bulrush, SCPJU).

Penoxsulam and glufosinate-ammonium, or an agriculturally acceptable salt or ester thereof, may be used to control herbicide resistant or tolerant weeds. The methods employing the combination of penoxsulam and glufosinate-ammonium, or agriculturally acceptable salt or ester thereof, and the compositions described herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

In some embodiments, the weight ratio of penoxsulam to glufosinate in the compositions and methods described herein lies within the range of 1:400 to about 3:1, and in another embodiment, from about 1:200 to about 1.5:1. In some embodiments, the weight ratio of penoxsulam to glufosinate-ammonium is from about 1:168 to about 1:1.4, and in another embodiment, from about 1:56 to about 1:1.

In some embodiments, the weight ratio of penoxsulam to glufosinate-ammonium is from about 1:1.75 to about 1:112. In embodiments, the weight ratio of penoxsulam to glufosinate-ammonium is from about 1:3.5 to about 1:56. In some embodiments, the weight ratio of penoxsulam to glufosinate-ammonium is from about 1:1.75 to about 1:112. In embodiments, the weight ratio of penoxsulam to glufosinate-ammonium is from about 1:3.5 to about 1:3.5 to about 1:14.

The rate at which the synergistic composition is applied will depend upon the particular type of weed to be controlled, the degree of control required, and the timing and method of application. The composition of the disclosure can be applied at an application rate from about 40 grams of active ingredient per hectare (gai/ha) to about 890 gai/ha based on the total amount of active ingredients in the composition. In one embodiment, penoxsulam is applied at a rate from about 2.5 g/ha to about 100 g/ha and glufosinate-ammonium is applied at a rate of about 17.5 g/ha to about 1700 g/ha. In another embodiment, penoxsulam is applied at a rate from about 5 g/ha to about 50 g/ha and glufosinate-ammonium is applied at a rate from about 35 g/ha to about 840 g/ha. In another embodiment, penoxsulam is applied at a rate from about 5 g/ha to about 20 g/ha and glufosinate-ammonium is applied at a rate from about 35 g/ha to about 280 g/ha.

The components of the synergistic mixture of the present disclosure can be applied either separately or as part of a multipart herbicidal system.

The synergistic mixture of the present disclosure can be applied in conjunction with one or more other herbicides to control a wider variety of undesirable vegetation. When used in conjunction with other herbicides, the composition can be formulated with the other herbicide or herbicides, tank-mixed with the other herbicide or herbicides, or applied sequentially with the other herbicide or herbicides. Some of the herbicides that can be employed in conjunction with the synergistic composition of the present disclosure include: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidonethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glyphoate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, choline salts, optically active isomers and mixtures thereof.

The synergistic composition of the present disclosure can, further, be used in conjunction with dicamba, imidazolinones, sulfonylureas, or 2,4-D on glyphosate-tolerant, dicamba-tolerant, imidazolinone-tolerant, sulfonylurea-tolerant and 2,4-D-tolerant crops. In one embodiment, the synergistic composition of the present disclosure is used in combination with herbicides that are selective for the crop being treated and which complement the spectrum of weeds controlled by these compounds at the application rate employed. In another embodiment, the synergistic composition described herein is applied at the same time, either as a combination formulation or as a tank mix, with other complementary herbicides.

In one embodiment, the synergistic composition of the present disclosure is used in mixtures containing a herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or can be tank mixed.

Suitable agricultural adjuvants and carriers that are useful in preparing the herbicidal mixtures of the composition described herein are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG(400) dioleate-99.

Liquid carriers that can be employed include water and organic solvents. The organic solvents used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In one embodiment, one or more surface-active agents are incorporated into the compositions of the present disclosure. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutyl-naphthalenesulfonate; dialkyl esters of sulfo-succinate salts, such as sodium di(2-ethylhexyl) sulfo-succinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters, including but not limited to, methyl esters of the above vegetable oils.

Some of these materials, such as vegetable or seed oils and their esters, can be used interchangeably as an agricultural adjuvant, as a liquid carrier or as a surface active agent.

Other additives used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In one embodiment, the concentration of the active ingredients in the synergistic composition of the present disclosure is from 0.1 to 98 percent by weight. In another embodiment, concentrations from 2 to 90 percent by weight are employed. In compositions designed to be employed as concentrates, the active ingredients are present in a concentration from 5 to 98 weight percent, and in another embodiment, from 10 to 90 weight percent. In one embodiment, such compositions are diluted with an inert carrier, such as water, before making a postemergence, foliar application to exposed weed and crop foliage, or applied as a dry or liquid formulation directly into flooded rice fields. The diluted compositions described herein that are applied as a postemergence, foliar application to weeds or the locus of weeds contain 0.05 to 10 weight percent active ingredient (ai) and, in another embodiment, contain 0.2 to 3.0 weight percent ai.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present disclosure.

EXAMPLE

Evaluation of Postemergence Herbicidal Activity of Mixtures under Field Conditions Methodology Field trials were conducted in rice using standard herbicide small plot research methodology. Plot size was 2 square meters ($m^2$) using 1.6 meter (m) diameter rings placed into the rice paddy soil with capability for flooding to maintain good rice cultural practices and rice growing conditions. There were 3 replicates per treatment. Rice was Japonica type that was sown as wet-seeded rice (pre-germinated) into the saturated soil in the rings as per normal cultural practices. The rice crop was grown using normal cultural practices for fertilization, seeding, watering, flooding and maintenance to ensure good growth of the crop and the weeds under seeded rice conditions in Taiwan. Ring plot water conditions were maintained under saturated soil conditions after planting. Just prior to treatment application, any remaining plot water was drained to maintain saturated soil in ring plot. Treatments were applied by backpack using compressed air at 30 pounds per square inch (psi) using Flat Fan nozzles at a spray volume of 450 Liters/hectare (L/ha). Penoxsulam was applied as the Fencer® 25OD formulation. Glufosinate-ammonium was applied as the Basta® 135 SL formulation.

All treatments in the field trials were applied by spraying the treatments on the rice and weeds and evaluated at 7, 14, or 28 days after application (DAA). Commercially available products of penoxsulam (FENCER 25OD) and glufosinate-ammonium (BASTA 135 SL) were mixed in water and sprayed onto the rice and weeds with the appropriate formulated product amounts to treat 2 m² to achieve the desired application rates based on unit area of application (hectare).

The treated and control plots were rated blind at various intervals after application, with the last evaluation taken 28 days after application. Ratings were based on percent (%) visual weed control, where 0 corresponds to no control and 100 corresponds to complete control. Results are reported in Tables 1 through 6.

Evaluation

Data was collected and analyzed using various statistical methods.

Colby's equation was used to determine the herbicidal effects expected from the mixtures (Colby, S. R. Calculation of the synergistic and antagonistic response of herbicide combinations. *Weeds* 1967 15, 20-22). Results are shown where P<0.05 according to Colby's method of analysis.

The following equation was used to calculate the expected activity of mixtures containing two active ingredients, A and B:

$$Expected = A + B - (A \times B / 100)$$

A=observed efficacy of active ingredient A at the same concentration as used in the mixture;
B=observed efficacy of active ingredient B at the same concentration as used in the mixture.

The results are summarized in Tables 1 through 6.

TABLE 1

Synergistic weed control of ECHCG at 14 Days After Application (DAA) following a postemergence application of Penoxsulam + Glufosinate-ammonium to wet-seeded rice.

| Penoxsulam | Glufosinate-ammonium | DAA | ECHCG (% Control) Obs* | Expected* |
|---|---|---|---|---|
| (grams ai/ha) | | | | |
| 5 | 0 | 14 | 53 | — |
| 0 | 35 | 14 | 0 | — |
| 5 | 35 | 14 | 62 | 53 |
| 10 | 0 | 14 | 62 | — |
| 0 | 35 | 14 | 0 | — |
| 10 | 35 | 14 | 77 | 62 |
| 10 | 0 | 14 | 62 | — |
| 0 | 70 | 14 | 0 | — |
| 10 | 70 | 14 | 85 | 62 |
| 10 | 0 | 14 | 62 | — |
| 0 | 140 | 14 | 27 | — |
| 10 | 140 | 14 | 87 | 72 |

TABLE 2

Synergistic weed control of ECHCG at 28 Days After Application (DAA) following a postemergence application of Penoxsulam + Glufosinate-ammonium to wet-seeded rice.

| Penoxsulam | Glufosinate-ammonium | DAA | ECHCG (% Control) Obs* | Expected* |
|---|---|---|---|---|
| (grams ai/ha) | | | | |
| 5 | 0 | 28 | 30 | — |
| 0 | 280 | 28 | 13 | — |
| 5 | 280 | 28 | 92 | 39 |
| 10 | 0 | 28 | 42 | — |
| 0 | 35 | 28 | 0 | — |
| 10 | 35 | 28 | 50 | 42 |
| 10 | 0 | 28 | 42 | — |
| 0 | 70 | 28 | 0 | — |
| 10 | 70 | 28 | 57 | 42 |
| 10 | 0 | 28 | 42 | — |
| 0 | 140 | 28 | 0 | — |
| 10 | 140 | 28 | 60 | 42 |
| 10 | 0 | 28 | 42 | — |
| 0 | 280 | 28 | 13 | — |
| 10 | 280 | 28 | 87 | 50 |
| 20 | 0 | 28 | 87 | — |
| 0 | 70 | 28 | 0 | — |
| 20 | 70 | 28 | 93 | 87 |

TABLE 3

Synergistic weed control of CYPDI at 14 Days After Application (DAA) following a postemergence application of Penoxsulam + Glufosinate-ammonium to wet-seeded rice.

| Penoxsulam | Glufosinate-ammonium | DAA | CYPDI (% Control) Obs* | Expected* |
|---|---|---|---|---|
| (grams ai/ha) | | | | |
| 5 | 0 | 14 | 73 | — |
| 0 | 35 | 14 | 0 | — |
| 5 | 35 | 14 | 93 | 73 |
| 5 | 0 | 14 | 73 | — |
| 0 | 70 | 14 | 0 | — |
| 5 | 70 | 14 | 93 | 73 |
| 5 | 0 | 14 | 73 | — |
| 0 | 140 | 14 | 0 | — |
| 5 | 140 | 14 | 93 | 73 |

TABLE 4

Synergistic weed control of MOOVA at 14 Days After Application (DAA) following a postemergence application of Penoxsulam + Glufosinate-ammonium to wet-seeded rice.

| Penoxsulam | Glufosinate-ammonium | DAA | MOOVA (% Control) Obs* | Expected* |
|---|---|---|---|---|
| (grams ai/ha) | | | | |
| 5 | 0 | 14 | 37 | — |
| 0 | 18 | 14 | 0 | — |
| 5 | 18 | 14 | 83 | 37 |
| 5 | 0 | 14 | 37 | — |
| 0 | 70 | 14 | 0 | — |
| 5 | 70 | 14 | 90 | 37 |

TABLE 5

Synergistic weed control of SCPJU at 7 Days After Application (DAA) following a postemergence application of Penoxsulam + Glufosinate-ammonium to wet-seeded rice.

| Penoxsulam | Glufosinate-ammonium | DAA | SCPJU (% Control) Obs* | Expected* |
|---|---|---|---|---|
| (grams ai/ha) | | | | |
| 5 | 0 | 7 | 40 | — |
| 0 | 18 | 7 | 0 | — |
| 5 | 18 | 7 | 80 | 40 |
| 5 | 0 | 7 | 40 | — |
| 0 | 35 | 7 | 0 | — |
| 5 | 35 | 7 | 85 | 40 |

TABLE 5-continued

Synergistic weed control of SCPJU at 7 Days After Application (DAA) following a postemergence application of Penoxsulam + Glufosinate-ammonium to wet-seeded rice.

| Penoxsulam | Glufosinate-ammonium | | SCPJU (% Control) | |
|---|---|---|---|---|
| (grams ai/ha) | | DAA | Obs* | Expected* |
| 5 | 0 | 7 | 40 | — |
| 0 | 140 | 7 | 0 | — |
| 5 | 140 | 7 | 92 | 40 |
| 20 | 0 | 7 | 92 | — |
| 0 | 70 | 7 | 0 | — |
| 20 | 70 | 7 | 99 | 92 |

TABLE 6

Synergistic weed control of SCPJU at 28 Days After Application (DAA) following a postemergence application of Penoxsulam + Glufosinate-ammonium to wet-seeded rice.

| Penoxsulam | Glufosinate-ammonium | | SCPJU (% Control) | |
|---|---|---|---|---|
| (grams ai/ha) | | DAA | Obs* | Expected* |
| 5 | 0 | 28 | 0 | — |
| 0 | 18 | 28 | 0 | — |
| 5 | 18 | 28 | 53 | 0 |
| 5 | 0 | 28 | 0 | — |
| 0 | 35 | 28 | 0 | — |
| 5 | 35 | 28 | 53 | 0 |
| 5 | 0 | 28 | 0 | — |
| 0 | 70 | 28 | 0 | — |
| 5 | 70 | 28 | 83 | 0 |
| 5 | 0 | 28 | 0 | — |
| 0 | 140 | 28 | 0 | — |
| 5 | 140 | 28 | 47 | 0 |

ECHCG—barnyard grass (*Echinochloa crus-galli*)
CYPDI—smallflower umbrella sedge (*Cyperus difformis*)
MOOVA—monochoria (*Monochoria vaginalis*)
SCPJU—Japanese bulrush (*Schoenoplectus juncoides*)
grams ai/ha—grams of active ingredient per hectare
Obs*—percent weed control observed
Expected*—percent weed control expected by Colby equation

What is claimed is:

1. A synergistic herbicidal composition comprising an herbicidally effective amount of penoxsulam and glufosinate-ammonium, wherein the weight ratio of penoxsulam to glufosinate-ammonium is from 1:3.5 to 1:56 and the composition includes no other herbicide.

2. The composition of claim 1, wherein the composition further comprises an agriculturally acceptable adjuvant or carrier.

3. The composition of claim 1, wherein the composition further comprises water.

4. The composition of claim 1, wherein the composition is synergistic as determined by the Colby equation.

5. A method of controlling undesirable vegetation comprising
   (a) contacting the vegetation or area adjacent to the vegetation with a synergistic herbicidal composition comprising a herbicidally effective amount of penoxsulam and glufosinate-ammonium, wherein the weight ratio of penoxsulam to glufosinate-ammonium is from 1:3.5 to 1:56 and the composition includes no other herbicide, or
   (b) pre-emergently applying the composition to soil or water.

6. The method of claim 5, wherein method comprises contacting the vegetation or area adjacent to the vegetation with the composition.

7. The method of claim 5, wherein method comprises pre-emergently applying the composition to soil or water.

8. The method of claim 5, wherein the undesirable vegetation is controlled in the group of crops and applications selected from the group consisting of rice, cereals, soybeans, cotton, sunflower, oilseed rape, vegetables, wheat, barley, oats, rye, sorghum, corn, maize, pastures, grasslands, rangelands, fallowland, turf, tree or vine orchards, aquatics, industrial vegetation management, and rights of way.

9. The method of claim 8, wherein the undesirable vegetation is controlled in rice.

10. The method of claim 5, wherein the undesirable vegetation is immature.

11. The method of claim 5, wherein in (a) or (b), the composition is applied to water.

12. The method of claim 11, wherein the water is part of a flooded rice paddy.

13. The method of claim 5, wherein the undesirable vegetation is selected from the group consisting of glyphosate-, glufosinate-, dicamba-, phenoxy auxins-, pyridyloxy auxins-, aryloxyphenoxypropionates-, acetyl CoA carboxylase (ACCase) inhibitors-, imidazolinones-, acetolactate synthase (ALS) inhibitors-, 4-hydroxyphenyl-pyruvate dioxygenase (HPPD) inhibitors-, protoporphyrinogen oxidase (PPO) inhibitors-, triazines-, and bromoxynil- tolerant crops.

14. The method of claim 13, wherein the tolerant crop possesses multiple or stacked traits conferring tolerance to multiple herbicides or inhibitors of multiple modes of action.

15. The method of claim 5 wherein the undesirable vegetation comprises a herbicide resistant or tolerant weed.

16. The method of claim 15, wherein the resistant or tolerant weed is a biotype with resistance or tolerance to multiple herbicides, multiple chemical classes, or inhibitors of multiple herbicide modes-of-action.

17. The method of claim 16, wherein the resistant or tolerant weed is selected from a group consisting of a biotype resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, and organoarsenicals.

18. The method of claim 5, wherein the undesirable vegetation is selected from a group consisting of Cyperus, Echinochloa, Monchoria, and Schoenoplecus vegetation.

19. The method of claim 5, wherein the undesirable vegetation is selected from a group consisting of *Cyperus difformis* L. (smallflower umbrella sedge), *Echinochloa crus-galli* (L.) Beauv. (barnyardgrass), monochoria (Monochoria vaginalis) and *Schoenoplectus juncoides* (Roxb.) Palla (Japanese bulrush).

20. A method of controlling undesirable vegetation comprising
   (a) contacting the vegetation or area adjacent to the vegetation with penoxsulam and glufosinate ammonium using a weight ratio of penoxsulam to glufosinate-ammonium of from 1:3.5 to 1:56;

or (b) applying penoxsulam and glufosinate ammonium to soil or water, wherein the penoxsulam and glufosinate ammonium is contacted or applied simultaneously or sequentially and the weight ratio of penoxsulam to glufosinate-ammonium is from 1:3.5 to 1:56 and wherein penoxsulam and glufosinate-ammonium are the only herbicides applied.

* * * * *